(12) United States Patent
Hood et al.

(10) Patent No.: US 6,582,658 B1
(45) Date of Patent: Jun. 24, 2003

(54) FIBER OPTIC MOISTURE SENSOR

(75) Inventors: Patrick J. Hood, Bellbrook, OH (US); Chrysa M. Theodore, Dayton, OH (US); Alison M. Yates, Dayton, OH (US)

(73) Assignee: Cornerstone Research Group, Inc., Dayton, OH (US)

( * ) Notice: Subject to any disclaimer, the term of this patent is extended or adjusted under 35 U.S.C. 154(b) by 358 days.

(21) Appl. No.: 09/598,738

(22) Filed: Jun. 21, 2000

Related U.S. Application Data
(60) Provisional application No. 60/140,219, filed on Jun. 22, 1999.

(51) Int. Cl.[7] .............................................. G01N 21/00
(52) U.S. Cl. ................... 422/58; 422/82.05; 422/82.08; 436/39; 436/166; 436/172
(58) Field of Search .............................. 436/39, 41, 111, 436/113, 134, 142, 166, 172; 422/82.11, 82.06, 82.07, 82.08, 52, 58, 82.05

(56) References Cited

U.S. PATENT DOCUMENTS

| | | |
|---|---|---|
| 5,250,095 A | 10/1993 | Sigel, Jr. et al. |
| 5,308,771 A | 5/1994 | Zhou et al. |
| 5,319,975 A | 6/1994 | Pederson et al. |
| 5,440,927 A | 8/1995 | Chu et al. |
| 5,694,806 A | 12/1997 | Martin et al. |
| 5,774,603 A | 6/1998 | Moore et al. |
| 5,995,686 A | 11/1999 | Hamburger et al. |

OTHER PUBLICATIONS

Zhou et al., "Porous Fiber–Optic Sensor for High–Sensitivity Humidity Measurements," *Analytical Chemistry*, vol. 60, No. 20, Oct. 15, 1988, (pp. 2317–2320).

L. Hench et al., "The Sol–Gel Process," *Chemical Reviews* vol. 90 No. 1, 1990, (pp. 33–72).

J. Ding et al., "Fiber Optic Moisture Sensors for High Temperatures," *Ceramic Bulletin*, vol. 70, No. 9, 1991, (pp. 1513–1517).

V. Ruddy, "Nonlinearity of Absorbance with Sample Concentration and Path Length in Evanescent Wave Spectroscopy Using Optical Fiber Sensors," *Optical Engineering*, vol. 33, No. 12, Dec. 1994, (pp. 3891–3894).

*Primary Examiner*—Jill Warden
*Assistant Examiner*—Samuel P. Siefke
(74) *Attorney, Agent, or Firm*—Wegman, Hessler & Vanderburg

(57) ABSTRACT

A fiber optic moisture sensor is described that can detect the presence or concentration of an analyte in an environment; additionally, a method for making the sensor is described. The invention consists of three primary components: a sensor head, an optical link, and a sensor readout. The sensor head contains the sensing medium, which is comprised of a superabsorbing polymer that hosts a hydrochromic material. The superabsorbing polymer attracts moisture from the environment it is sensing until an equilibrium concentration of water in the environment is obtained effectively magnifying the ability of the hydrochromic material to sense very small concentrations of moisture. An optical link allows light to travel to and from the sensor head. The sensor readout has the necessary electronics to calibrate the optical signal from the sensor head, and the ability to determine and communicate the moisture concentration in the environment being sensed to the user or process control system.

29 Claims, 6 Drawing Sheets

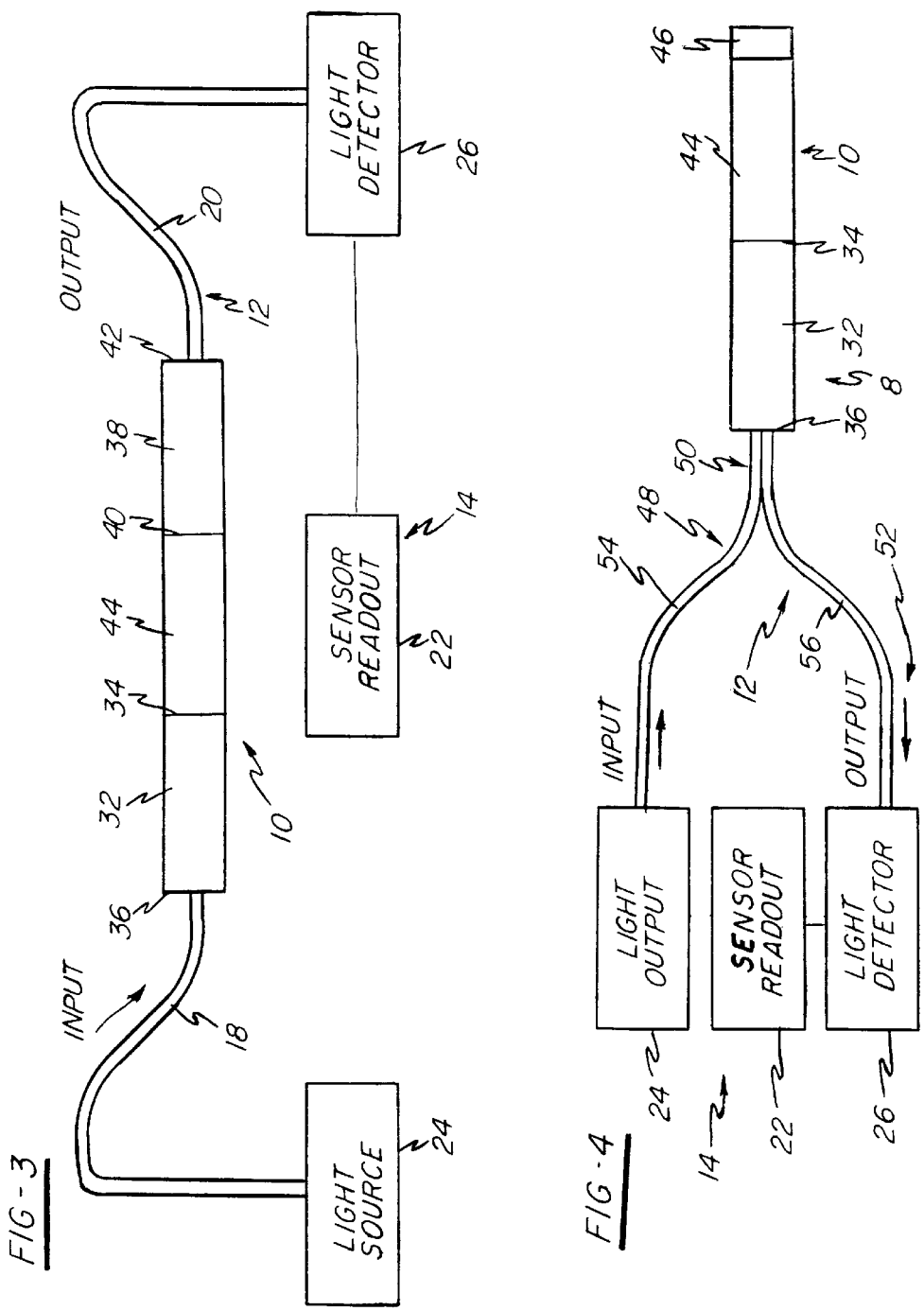

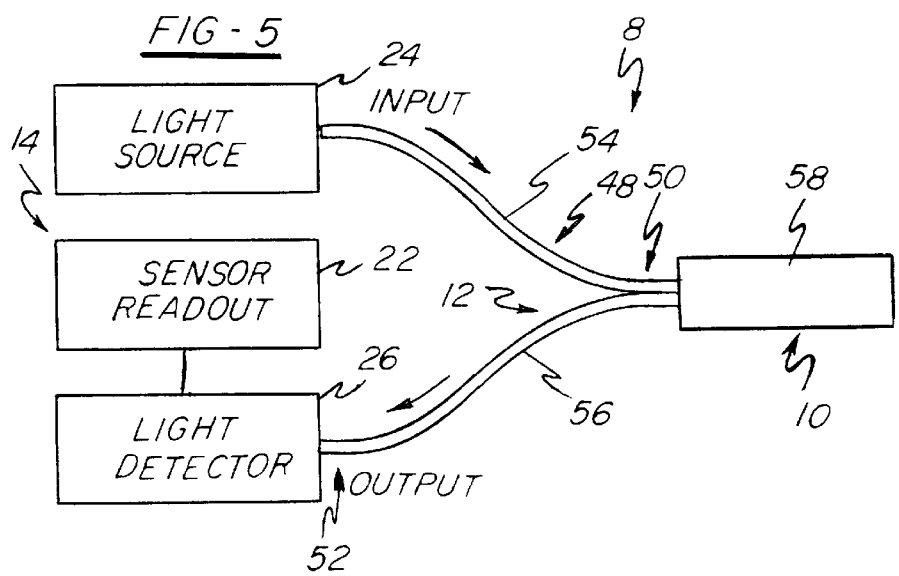
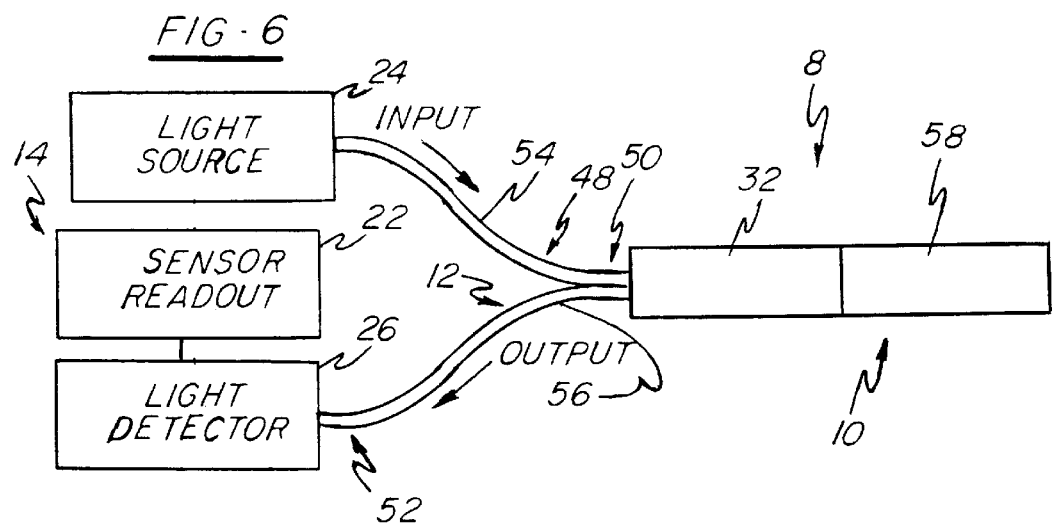

FIBER OPTIC MOISTURE SENSOR

CROSS-REFERENCE TO RELATED APPLICATION

This application claims the benefit of U.S. Provisional Patent Application Serial No. 60/140,219 filed Jun. 22, 1999.

BACKGROUND OF THE INVENTION

A plethora of sensors exist to indicate the presence or concentration of an analyte in a fluid or gas. Over the past years, different types of fiber optic moisture sensors have been developed. This detection of moisture is important in many industries and is especially useful in many applications in which free water is not present.

Generally, moisture sensors have a sensor head comprising a sensing material, an appropriate optical link, and a sensor readout. Sensing of the moisture is achieved by interaction of the water molecules with the sensing material. The optical link transmits light from a light source to the sensing material. The resulting optical signal is relayed to a light detector via the optical link so that a sensor readout can determine the concentration of the water in the environment being sensed.

Fiber optic sensors typically fall into one of the following four modes of sensors: transmissive sensors, porous fiber sensors, tip-coated (reflection) sensors, and side-coated (evanescent) sensors.

Transmission-mode sensors utilize two waveguides. The first launches light into the sensing medium or the fluid being tested and is collected by a second waveguide. The sensing medium is doped with a calorimetric or fluorescent compound that undergoes optical changes in the presence of the analyte being sensed. This type of mode is extremely inefficient and lossy due to the lack of optical couplings between the waveguides and the sensing medium.

A porous fiber sensor is made by altering the fiber core. In this mode of sensor, light propagates through the altered fiber core which has been doped with a water indicator. For example, U.S. Pat. No. 5,250,095 to Sigel, Jr., et al. began with a fiber of alkali borosilicate glass, a small section of which was heat treated to cause phase separation, resulting in a silica rich phase and an alkali borate rich phase. The latter was leached away, leaving only a porous silica core. The sensor is created by immersing the treated portion of the fiber in a solution containing an indicator. Due to the specially drawn fibers and chemical processing, this mode of sensor is costly and exhibits a slow response time.

In a reflective sensor, the fiber launches light onto a reflective or scattering sensing medium. Retroreflected light is collected by the same or an adjacent fiber. Reflection sensors are constructed either by coating the tip of the fiber with a cladding and indicator, then attaching a reflective film, or by coating a reflective surface with the indicator, then affixing the surface to the fiber end. The device may consist of either a bifurcated fiber, or a single fiber with a beam splitter, which separates the transmitted and detected rays. This mode of fiber sensor is fairly lossy.

The phenomenon of evanescence has frequently been employed to create sensors. In an evanescent sensor, light that is propagated down the waveguide is lost to the environment which is being sensed. The loss occurs over a length of the fiber that has a special cladding doped with an indicator. The cladding, made of materials such as sol-gel or electrostatic self-assembly (ESA) bilayers, has a higher index of refraction than the fiber core, causing the cladding to become the waveguide over the particular length of fiber. The light interacts with the indicator in the sensing medium, and as moisture is absorbed, the optical properties of the indicator change, changing the absorption of the spectrum. Evanescent-mode sensors require much processing and are typically very time-consuming to fabricate. Because the indicator is only present in the cladding, evanescent sensors lack desirable sensitivity.

Moisture sensors with sensor heads comprising superabsorbent polymers attached to a support substrate have also been employed. The superabsorbent polymer chemically binds a sensing reagent. Water from the sensed environment diffuses into the superabsorbent polymer until equilibrium is reached while the water molecules bond to the sensing reagent to change the optical quality of the polymer which is detected by a sensor readout.

Currently, superabsorbent polymers are placed on a support housing, or around glass support beads, or upon or around other means for support to form what generally can be called the sensor head in fiber optic moisture sensors. These means for support dictate against a direct optical connection of the polymer to the light source or light detector. As such, the general problems encountered with these sensors have been associated with the optical and physical coupling of optical links to the polymeric sensing elements, contributing to poor stability and reproducibility of results.

Therefore, it is one object of the invention to formulate a self-supporting optical quality superabsorbent polymer for use as the sensor head of a fiber-optic moisture sensor such that there can be direct physical and optical communication between the sensor head and an optical link allowing for accurate and reproducible results.

SUMMARY OF THE INVENTION

The described invention detects the presence of either low concentrations or high concentrations of water in an environment and consists of three primary components: a sensor head, an optical link, and a sensor readout.

The sensor head contains a sensing medium. The sensing medium in this invention is based on what is commonly referred to as a superabsorbing polymer, or hydrogel, doped with a hydrochromic material, otherwise generally know as a moisture sensing reagent. The superabsorbing polymer is hydrophilic (amenable to absorbing water) and serves as host for the hydrochromic material and propagates light along its length thereby acting as a waveguide.

The superabsorbing polymer composition of this invention creates an optical quality sensing media host which is self-supporting. Due to the versatility and strength of the superabsorbing polymer, it may be cast into a number of different satisfactory shapes (eg. fiber or cylinder) for use in a fiber optic moisture sensor, as such, the need for support means like a support housing or support beads is avoided. The self-supporting superabsorbing polymer may also be cast as a wave guide or light pathway on a photonic chip or the like.

The artisan will appreciate that one or more gradient index lenses may be adjoined to the superabsorbent polymer thereby directing a collimated beam of light through the polymer. Also, the artisan will appreciate that the sensor head further may consist of a reflective mirror which directs transmitted light back through the superabsorbent polymer to the transmitting optical link. In any of these configurations, the polymer is directly adjoined to whatever may be adjacent (eg. optical link, gradient index lenses, mirror) thereby maintaining quality optical transmissions.

Because the superabsorbing polymer is extremely hydrophilic, it will attract moisture from the environment it is sensing. This characteristic of attracting moisture increases the equilibrium concentration of water in the polymer thereby effectively magnifying the ability of the hydrochromic material to sense very small concentrations of moisture in the environment.

The preferred composition in accordance with the self-supporting superabsorbent polymer of this invention comprises a mixture of an acrylate resin, a polyacrylamide, a polymerization initiator, and at least one solvent. Preferably, the acrylate resin comprises 96% pure 2-hydroxyethyl acrylate, the polyacrylamide comprises 99% pure N,N'-methylenebisacrylamide, the polymerization initiator comprises 2,2'-Azobis(2-(2-imidazolin-2-yl)propane) dihydrochloride, and the solvent comprises deionized water. Most preferably, 96% pure 2-hydroxyethyl acrylate comprises 27–43% by weight of the composition, 99% pure N,N'-methylenebisacrylamide comprises 0.27%–0.42% by weight of the composition, deionized water comprises 56–72% by weight of the composition, and 2,2'-Azobis(2-(2-imidazolin-2-yl)propane) dihydrochloride comprises 0.02%–0.04% by weight of the composition.

As stated above, the superabsorbent material is doped with, or plays host to, a hydrochromic material. It is anticipated that there are many hydrochromic materials that can be used in this invention. This hydrochromic material may consist of various salts as well as polymer dyes. Preferably, the hydrochromic material comprises cobalt chloride or copper chloride. Cobalt chloride is most preferred. The amount of hydrochromic material used is 0.000005–0.06 grams per ml of deionized water. The actual concentration is strongly dependent on which hydrochromic material is used and for what range of moisture the sensor is designed to detect.

The self-supporting superabsorbent polymer constituents and the hydrochromic material is synthesized to form the doped self-supporting superabsorbent polymer useful in a fiber optic moisture sensor.

The next component, the optical link, is the means for transmitting light to and from the sensor head. This means for transmitting light includes at least one optical fiber by which light can be input to and output from the sensor head. As such, the optical link may comprise separate input and output optical fibers, one bifurcated optical fiber with branched input and output fibers, or some other variation thereof. Transparent optical fibers are most preferred. The optical link is adjoined to the sensor head such that there can be direct optical communication.

Lastly, the sensor readout is operatively associated with at least one light source and at least one light detector in optical communication with the optical link. In addition, the sensor readout has the necessary electronics to calibrate the optical signal from the sensor head to be able to determine the concentration of moisture in the environment. Finally, the sensor readout has some way of displaying or communicating the moisture concentration in the environment being sensed to the user or process control system.

By synthesizing the above described chemical compounds, we have been able to formulate a self-supporting superabsorbent polymer of excellent optical quality for use in a sensor head. This superabsorbent polymer may be cast as a fiber or cylinder, or as some other useful element, and does not require any support means as previously needed in fiber optic moisture sensors. It acts as the wave guide itself as opposed to prior art devices wherein the photons were carried along another light transport media such as a glass fiber or glass bead that served as a support substrate for the polymer. The superaborsent polymer may therefore be adjoined directly to an optical link thereby making possible a stable high-sensitivity, low-concentration moisture sensor with accurately reproducible results.

In a preferred embodiment of the invention, the sensor head of a fiber optic moisture sensor comprises a doped, optically transparent self-supporting superabsorbing polymer cast as a fiber. In another embodiment, the self-supporting superabsorbent polymer is opaque or optically non-transparent, as such, the polymer is described as a scattering superabsorbent polymer. The opaque nature of the self-supporting superabsorbent polymer allows for the use of a wider range of superabsorbent polymer materials in forming the self-supporting superabsorbent polymer.

In light of the above, it is an object of this invention to provide an optical sensor to sense water content in fluids.

It is an object of this invention to provide a self-supporting superabsorbing polymer integrated with a hydrochromic material as the sensing device.

It is an object of this invention to provide a reliable sensor with reproducible and repeatable results.

It is an object of this invention to provide a low-cost sensor that can easily be integrated into existing industrial systems.

It is an object of this invention to provide a method for making the sensor.

Other objects and advantages of the invention will be apparent from the following description, the accompanying drawings and the appended claims.

BRIEF DESCRIPTION OF THE DRAWINGS

FIG. 3 is a schematic of a second embodiment for a fiber optic moisture sensor showing a lens coupled sensor head;

FIG. 4 is a schematic of a third embodiment for a fiber optic moisture sensor showing a lens coupled sensor head with a reflective mirror;

FIG. 5 is a schematic of a fourth embodiment for a fiber optic moisture sensor showing a scattering self-supporting superabsorbent polymer sensor head;

FIG. 6 is a schematic of a fifth embodiment for a fiber optic moisture sensor showing a lens coupled scattering sensor head;

DETAILED DESCRIPTION OF THE PREFERRED EMBODIMENT

Figure 1:
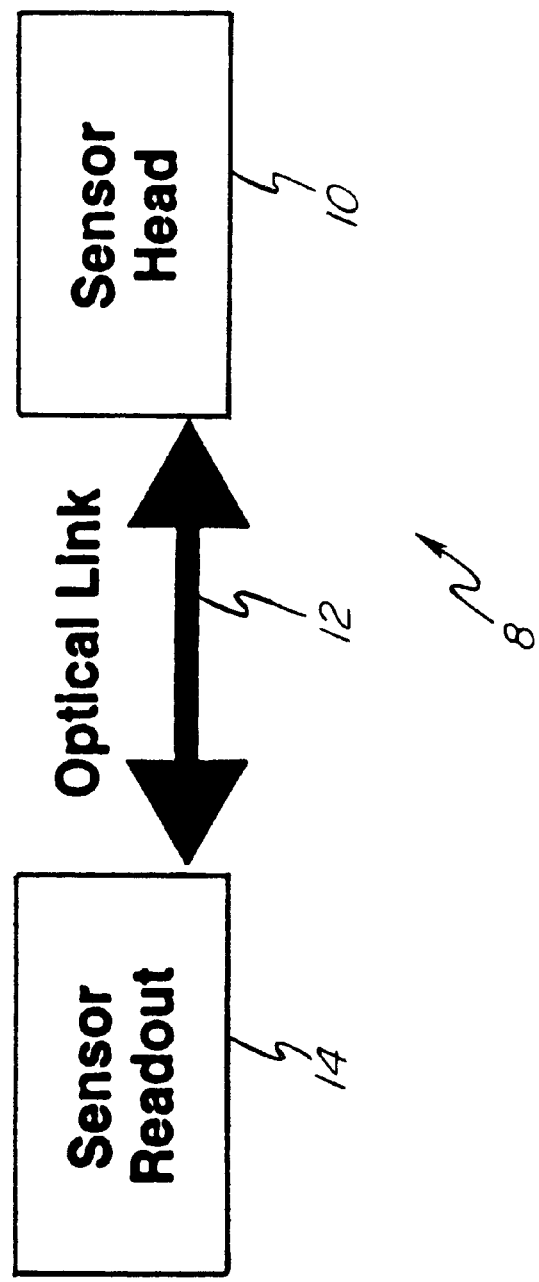
FIG. 1 shows a block diagram of this invention including the following: sensor head, optical link, and sensor readout.

As shown in FIG. 1, this invention, or fiber optic moisture sensor 8, consists of three primary components: a sensor head 10, an optical link 12, and a sensor readout 14.

The sensor head 10 contains a self-supporting supersabsorbent polymer doped with a hydrochromic material. The polymer itself acts as the light waveguide in the sensor head as the light propagates through the analyte medium.

As to the super absorbing polymers that may be used in the invention, these include hydrophilic polymers comprising repeat units obtained via polymerization of acrylamide monomers and/or acrylate monomers such as hydroxylated lower alkyl ($C_1$–$C_6$) acrylates, and hydroxylated lower alkyl ($C_1$–$C_6$) (meth)acrylates. Also, hydrogel polymers such as those referred to in U.S. Pat. No. 5,694,806 (Mantis et al.) incorporated by reference herein are also within the ambit of the phrase super absorbent polymer as used herein.

In accordance with the '806 patent, exemplary hydrogel polymers are based on poly (ethylene oxide). Isocyanate terminated poly (ethylene oxide) polymers are commercially available and comprise, for example, poly(ethylene oxide) and poly(propylene oxide) repeat unit segments connected by polyurethaneurea segments.

The preferred self supporting polymer composition in accordance with the invention comprises a cross-linked polymer composed of repeat units formed from polymerization of 2-hydroxy ethyl acrylate monomer. Specifically, the polymer comprises a mixture of an acrylate resin, a polyacrylamide, a polymerization initiator, and at least one solvent. Preferably, the acrylate resin comprises 96% pure 2-hydroxyethyl acrylate. The polyacrylamide comprises 99% pure N,N'-methylenebisacrylamide as a cross linker. The polymerization initiator comprises 2,2'-Azobis(2-(2-imidazolin-2-yl)propane) dihydrochloride, and the solvent comprises deionized water. Most preferably, 96% pure 2-hydroxyethyl acrylate comprises 27–43% by weight of the composition, 99% pure N,N'-methylenebisacrylamide comprises 0.27%–0.42% by weight of the composition, deionized water comprises 56–72% by weight of the composition, and 2,2'-Azobis(2-(2-imidazolin-2-yl)propane) dihydrochloride comprises 0.02%–0.04% by weight of the composition.

The hydrochromic material may consist of various salts as well as polymer dyes. Preferably, the hydrochromic material comprises cobalt chloride or copper chloride of which cobalt chloride is most preferred. The amount of hydrochromic material used is 0.000005–0.06 grams per ml of said deionized water. The actual concentration of hydrochromic material is strongly dependent on which hydrochromic material is used and for what range of moisture the sensor is designed to detect.

The self-supporting superabsorbent polymer constituents are mixed along with the hydrochromic material to synthesize a doped self-supporting superabsorbent polymer used in the sensor head 10 of a fiber optic moisture sensor 8. Using the most preferred chemical constituents as an example, three solutions are conveniently prepared and mixed in the synthesis process to generate an optical quality, doped transparent self-supporting superabsorbing polymer. The artisan will appreciate that the following process can be used to create optically non-transparent, as well as, optically transparent superabsorbent polymers both of which may be used in sensor heads.

EXAMPLE 1

Solution #1: Dissolve dihydrochloride in deionized water by sonicating until dissolved—approximately 5–10 minutes.

Solution #2: Dissolve N,N'-methylenebisacrylamide in 2-hydroxyethyl acrylate by sonicating until dissolved—approximately 20–30 minutes.

Solution #3: Dissolve hydrochromic material into deionized water by sonicating until dissolved—approximately 5–10 minutes.

The superabsorbing material is synthesized using the following process. Solution #1 and Solution #2 are mixed thoroughly and then transferred into a mold heated to a temperature between 60–120° C. and placed in an oven for between 1–12 hrs. This generates a wet gel that can be removed from the mold. This gel is then soaked in pure deionized water for 1–48+ hours to remove unreacted monomer. The hydrochromic material is then added to the fully-saturated superabsorbent material by soaking it in Solution #3 for 24–48+ hours to allow equilibrium to be reached.

The saturated, doped gel is then removed from Solution #3 and placed in a non-airtight container to allow for gradual drying of the gel. Drying the gel too quickly results in optical defects and cracks in the bulk of the material. The process takes between 24–96 hours depending on the thickness of the optical component being dried. Once the majority of the water has been removed from the doped superabsorbent polymer it can be air dried at room temperature for an additional period of time, approximately 48 hours. Finally, the material can be oven dried at 60–120° C. for approximately 12 hours to drive off any residual water. It is necessary to heat the material to above 100° C. to ensure a fully dry sample that can sense very low concentrations of water.

An alternative approach for the addition of hydrochromic material into the optical element is to utilize Solution #1 as the solvent for the hydrochromic material. This hydrochromic material-deionized water solution (Solution #4) would replace Solution #1, and would eliminate the need to exchange the hydrochromic material into the superabsorbent polymer. This change would also necessitate eliminating the soaking step to remove unreacted monomer, since soaking would rinse the hydrochromic material from the polymer.

After the synthesis process is completed an optical quality, doped self-supporting superabsorbent polymer is formed which is ready to be used in a fiber optic moisture sensor to detect the moisture concentration of a specific environment.

The fiber optic moisture sensor 8 of this invention has five preferred embodiments. In each configuration light is sent into the doped, self-supporting superabsorbent polymer and then collected. Embodiments one, two, and three illustrate the use of a transparent self-supporting superabsorbent polymer in a fiber optic moisture sensor. The fourth and fifth embodiments illustrate the use of an optically non-transparent self-supporting superabsorbent polymer in a fiber optic moisture sensor.

Figure 2:
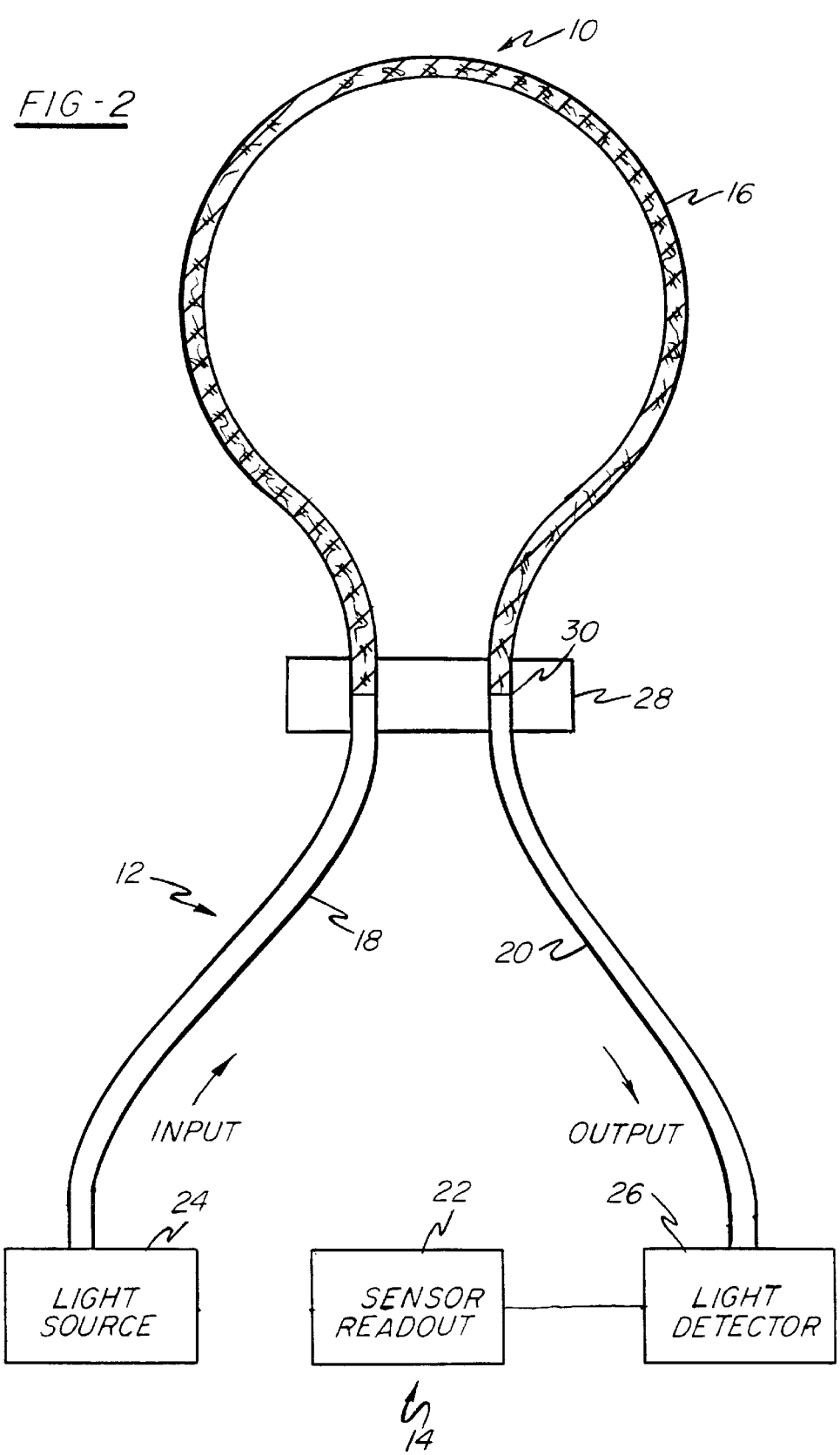
FIG. 2 is a schematic of a first embodiment for a fiber optic moisture sensor showing a fiber cast self-supporting superabsorbent polymer sensor head.

The first embodiment, illustrated in FIG. 2, consists of a fiber cast, doped, optically transparent self-supporting superabsorbent polymer 16, a transparent input optic fiber 18, a transparent output optic fiber 20, and a sensor readout 22 operatively associated with at least one light source 24 and at least one light detector 26. The optically transparent self-supporting superaborbant polymer fiber 16 is centrally located between and adjoined to the transparent input and output optic fibers (18, 20) and, as shown, serves as the sole wave guide in the sensor head, propagating light from optic fiber 16 to optic fiber 18. The light traveling through the transparent input optic fiber 18 from the light source 24 is attenuated proportionally with the relative moisture level in the environment. The light travels from the input optic fiber 18 through the optically transparent superabsorbent polymer fiber 16, the transparent output optic fiber 18, and finally to the light detector 26 so that the sensor readout 22 can determine the moisture concentration of the environment being sensed.

A variety of light sources such as light emitting diodes, laser diodes, etc. may be used as a light source. Presently, we are using a W-halogen white light source available from Ocean Optics, Dunedin, Fla. With regard to the light detectors, a variety of photodetectors can be used. At present, a spectrophotometer from Ocean Optics is used.

This first embodiment (FIG. 2) of a fiber optic moisture sensor 8 will have the fastest response time of any of the other embodiments. Although not critical to the optical functionality of the device, a splice coupling 28 can provide mechanical integrity to the fiber splice 30 between the transparent input and output optical fibers (18, 20) and the optically transparent self-supporting superabsorbent fiber 16.

The second embodiment, shown in FIG. 3, consists of a first gradient index lens 32 having a first and second end (34, 36), a second gradient index lens 38 having a first and second end (40, 42), and a cylinder cast, doped, optically transparent self-supporting superabsorbent polymer 44 centrally located between and adjoined to the first end 34 of the first and second gradient index lenses (32, 38). Further, a transparent input and output optic fiber (18, 20) respectively are adjoined to the second ends (36, 42) of the first and second gradient index lenses (32, 38) such that there is direct optical communication. A light source 24 and at least one light detector 26 are in optical communication with the input and output optic fibers (18, 20). A sensor readout 22 is operatively associated with the detector.

In this embodiment (FIG. 3), light is launched from the light source 24 to the transparent input optic fiber 18. From the transparent input optic fiber 18, a collimated beam is sent through the first gradient index lens 32. This collimated beam of light passes through the self-supporting superabsorbent polymer 44, collected by the second gradient index lens 38, and transmitted to the transparent output optic fiber 20. Finally, the light travels to the light detector 26 so that the sensor readout 22 can determine the moisture concentration of the environment being sensed.

In a third embodiment, as shown in FIG. 4, an inwardly facing reflective mirror 46 replaces the second gradient index lens 38 in FIG. 3. The mirror 46 is adjoined to the self-supporting superabsorbent polymer 44. Also, the transparent input and output optic fibers (18, 20) are replaced in FIG. 3 with a transparent bifurcated optic fiber 48 having a distal end 50 adjoined to the second end 36 of the first gradient index lens 32, and having a proximal end 52 with an input optic fiber 54 and an output optic fiber 56. The input optic fiber 54 is in optical communication with the light source 24 and the output optic fiber 56 is in optical communication with the light detector 26.

In this third embodiment (FIG. 4), light is directed to the superabsorbent polymer 44 via the input optic fiber 54. The light is reflected off the mirror 46 back to the transparent bifurcated fiber 48. The light finally travels to the light detector 26 so that the sensor readout 22 can determine the moisture concentration of the environment being sensed. The artisan will appreciate that the light can be collected in either the output or input optic fiber (56, 54).

The fourth and fifth embodiments, as shown in FIGS. 5 and 6, illustrate the use of an optically non-transparent self-supporting superabsorbent polymer 58. In FIG. 5, the fourth embodiment of the fiber optic moisture sensor 8 functions in a scattering mode using a scattering, optically non-transparent self-supporting superabsorbent polymer 58 cast as a cylinder. A transparent bifurcated optic fiber 48 having a distal end 50 is adjoined to the optically non-transparent self-supporting superabsorbent polymer 58. The transparent bifurcated optic fiber 48 further has a proximal end 52 with an input and output optic fiber (54, 56). The input optic fiber 54 is in optical communication with the light source 24 and the output optic fiber 56 is in optical communication with the light detector 26.

In FIG. 6, the fifth embodiment differs from the fourth embodiment (FIG. 5) in that a first gradient index lens 32 is centrally located between and adjoined to the optically non-transparent self-supporting superabsorbent polymer 58 and the distal end 50 of the transparent bifurcated optic fiber 48 of FIG. 5.

In this fourth and fifth embodiment, light is directed to the scattering self-supporting superabsorbent polymer 58 via the input optic fiber 54. The artisan will appreciate that retroreflected light from the scattering self-supporting superabsorbent polymer 58 can be collected in either the output or input optic fiber (56, 54). The light finally travels to the light detector 26 so that the sensor readout 22 can determine the moisture concentration of the environment being sensed.

Figure 7:
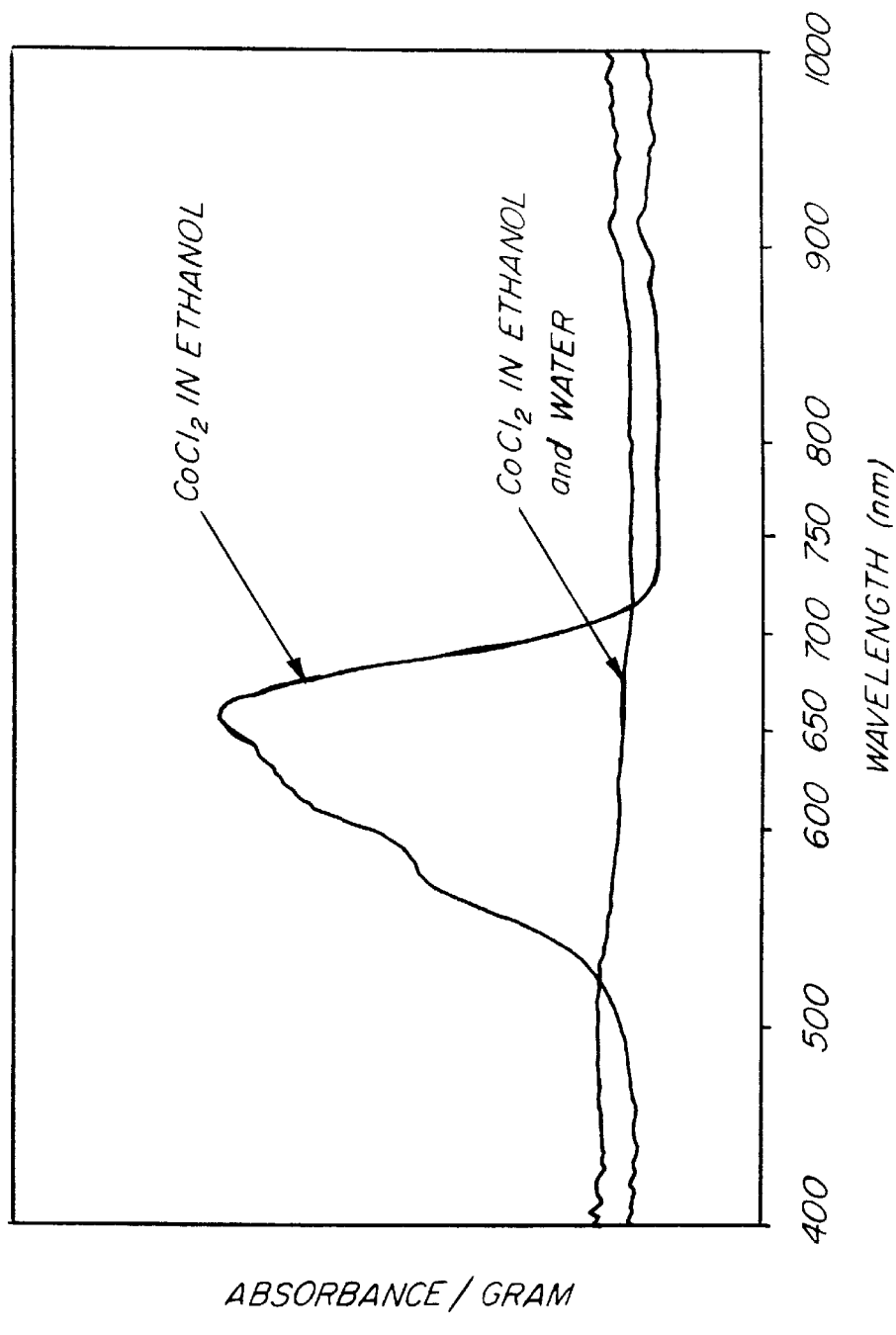
FIG. 7 shows the visible absorption per gram spectrum of cobalt chloride isolated from water and in the presence of water.

In each of the embodiments presented in this invention disclosure, the light collected by the output optic fiber (20, 56) is proportional to the moisture in the environment. The magnitude of the light absorption is also strongly dependent on the wavelength of the light being used. To illustrate. FIG. 7 shows the absorbance/gram of $CoCl_2$ (cobalt chloride) suspended in ethanol and also in a water/ethanol mixture. If one is using $CoCl_2$ as a sensing reagent, light at 650-nm is strongly attenuated in dry environment and not attenuated under damp conditions. This is not the case for 750-nm light. This means that a ratio of the signal intensity at these two wavelengths can be used to eliminate many of signal processing errors associated with calibrating moisture to the absolute magnitude of a transmitted light.

Modifying the concentration of the sensing reagent in the sensing medium will alter the sensitivity of the device. A high concentration will have more drastic changes in the intensity of the light collected when a large amount of moisture is absorbed, but very little change with small differences in humidity. When it is necessary to have high sensitivity, for example, in the 0%–10% relative humidity range, the concentration of the sensing reagent in the self-supporting superabsorbent polymer will be relatively low. If an application requires higher sensitivity in the upper regime, the concentration should be much greater. A wide range sensor can be fabricated by grading the concentration of the sensing material along the line length of the device.

Figure 8:
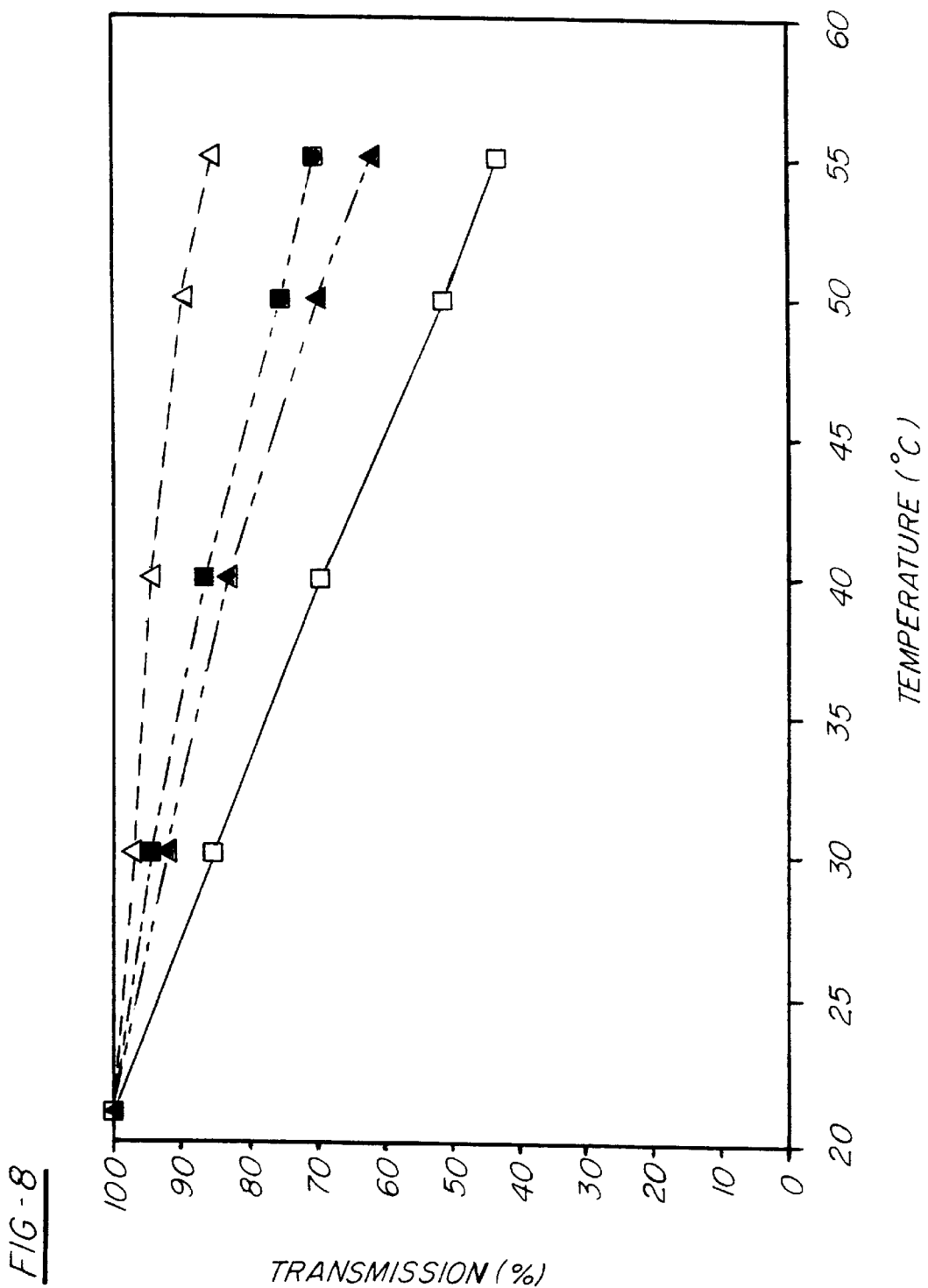
FIG. 8 shows the temperature dependence of the fiber optic moisture sensor at 676 nm for 4 different humidities.

The temperature dependence of a fabricated fiber optic moisture sensor at a single wavelength (676 nm) is shown in FIG. 8. The experiments were performed with air as the sensed environment. The relative humidities for each sequence are as follows: 28% 1, 30% 2, 36% 3, and 47% 4. The concentration of the hydrochromic material or sensing reagent is in a mid-range, thus a greater change in transmission is observed in the 20–30% range of humidities.

As is apparent, the superabsorbent fibers are "directly connected" to the fiber optics 18, 20 (FIG. 1). The joint formed, as shown in FIG. 1 can simply be an intimate contact butt joint wherein the requisite ends of the superabsorbent, waveguide, fiber is secured against the corresponding butt end of the optical fiber. This joint may be secured via clamps or other conventional means. Also, the joint can be secured by optical adhesives that are available from a variety of suppliers such as Norland Optical Adhesives, New Brunswick, N.J.; or Summers Optical Adhesives, Fort Washington, Pa.

While the form of apparatus and methods of making herein described constitutes a preferred embodiment of this invention, it is to be understood that the invention is not limited to this precise form of apparatus and method of making, and that changes may be made therein without departing from the scope of the invention which is defined in the appended claims.

What is claimed is:

1. A fiber optic moisture sensor comprising:

a sensor head having a self-supporting superabsorbent polymer therein;

means for transmitting light to and from said sensor head, said means for transmitting light adjoined to said sensor head, said sensor head being in direct optical communication with said means for transmitting light; and at least one light detector in optical communication with said means for transmitting light, said self supporting superabsorbent polymer supporting itself and said sensor head being devoid of any further support means.

2. The fiber optic moisture sensor as recited in claim 1 wherein said self-supporting superabsorbent polymer is the sole waveguide propagating light in said sensor head.

3. The fiber optic moisture sensor recited in claim 1, wherein said self-supporting superabsorbent polymer is cast as a fiber.

4. The fiber optic moisture sensor recited in claim 1, wherein said self-supporting superabsorbent polymer is cast as a cylinder.

5. The fiber optic moisture sensor as recited in claim 1 wherein said superabsorbent polymer is a member chosen from acrylamides, acrylates, (meth)acrylates, and hydrogels.

6. The fiber optic moisture sensor recited in claim 1, wherein said self-supporting superabsorbent polymer comprises a cross-linked acrylate resin.

7. The fiber optic moisture sensor as recited in claim 1 wherein said superabsorbent polymer comprises an acrylate resin, a polyacrylamide, a polymerization initiator, at least one solvent, and a hydrochromic material.

8. The fiber optic moisture sensor recited in claim 7, wherein said acrylate resin comprises 96% pure 2-hydroxyethyl acrylate, said polyacrylamide comprises 99% pure N,N'-methylenebisacrylamide, said polymerization initiator comprises 2,2'-Azobis(2-(2-imidazolin-2-yl) propane) dihydrochloride, said solvent comprises deionized water, and said hydrochromic material comprises cobalt chloride.

9. The fiber optic moisture sensor recited in claim 8, wherein said 96% pure 2-hydroxyethyl acrylate comprises 27–43% by weight composition, said 99% pure N,N'-methylenebisacrylamide 0.27%–0.42% by weight composition, said 2,2'-Azobis(2-(2-imidazolin-2-yl) propane) dihydrochloride comprises 0.02%–0.04% by weight composition, said deionized water comprises 56–72% by weight composition, and said cobalt chloride comprises 0.000005–0.06 grams per ml of said deionized water.

10. The fiber optic moisture sensor recited in claim 1, wherein said self-supporting superabsorbent polymer is optically transparent.

11. The fiber optic moisture sensor recited in claim 1, wherein said self-supporting superabsorbent polymer is optically non-transparent.

12. A fiber optic moisture sensor comprising:

a sensor head having a self-supporting superabsorbent polymer therein;

a means for transmitting light to and from said sensor head, said means for transmitting light adjoined to said sensor head, said sensor head being in direct optical communication with said means for transmitting light; and at least one light detector in optical communication with said means for transmitting light, said self-supporting superabsorbent polymer being optically non-transparent and wherein said sensor head further comprises a gradient index lens centrally located between and adjoined to said optically non-transparent self-supporting superabsorbent polymer and to said means for transmitting light such that said gradient index lens is in direct optical communication with said sensor head and said means for transmitting light.

13. A fiber optic moisture sensor comprising:

a sensor head having a self-supporting superabsorbent polymer therein;

a means for transmitting light to and from said sensor head, said means for transmitting light adjoined to said sensor head, said sensor head being in direct optical communication with said means for transmitting light; and at least one light detector in optical communication with said means for transmitting light, wherein said sensor head further comprises a first gradient index lens having first and second ends and a second gradient index lens having first and second ends, said self-supporting superabsorbent polymer being centrally located between and adjoined to said first end of said first gradient index lens and said first end of said second gradient index lens, and said second end of said first gradient index lens and said second end of said second gradient index lens adjoined to said means for transmitting light such that said first gradient index lens and said second gradient index lens are in direct optical communication with said self-supporting superabsorbent polymer and said means for transmitting light.

14. A fiber optic moisture sensor comprising:

a sensor head having a self-supporting superabsorbent polymer therein;

a means for transmitting light to and from said sensor head, said means for transmitting light adjoined to said sensor head, said sensor head being in direct optical communication with said means for transmitting light; and at least one light detector in optical communication with said means for transmitting light, wherein said sensor head further comprises a gradient index lens and a reflective mirror such that said self-supporting superabsorbent polymer is centrally located between and adjoined to said gradient index lens and said reflective mirror such that said gradient index lens is in direct optical communication with said means for transmitting light and said self-supporting superabsorbent polymer, said reflective mirror facing inwardly toward said self-supporting superabsorbent polymer thereby directing light back through said superabsorbent polymer and said gradient index lens to said means for transmitting light.

15. A fiber optic moisture sensor comprising:

a sensor head having an optically transparent self-supporting superabsorbent polymer fiber disposed in said sensor head;

a means for transmitting light to and from said sensor head, said means for transmitting light being in direct optical communication with said sensor head; and at least one light detector in optical communication with said means for transmitting light, said self supporting superabsorbent polymer fiber supporting itself and said sensor head being devoid of any further support means.

16. The fiber optic moisture sensor as recited in claim 15 wherein said self-supporting superabsorbent polymer is the sole waveguide propagating light in said sensor head.

17. The fiber optic moisture sensor as recited in claim 15, wherein said self-supporting superabsorbent polymer comprises an acrylate resin, a polyacrylamide, a polymerization initiator, at least one solvent, and hydrochromic material.

18. The fiber optic moisture sensor as recited in claim 17, wherein said acrylate resin comprises 96% pure 2-hydroxyethyl acrylate, said polyacrylamide comprises 99% pure N,N'-methylenebisacrylamide, said polymerization initiator comprises 2,2'-Azobis(2-(2-imidazolin-2-yl)propane) dihydrochloride, said solvent comprises deionized water, and said hydrochromic material comprises cobalt chloride.

19. The fiber optic moisture sensor as recited in claim 18, wherein said 96% pure 2-hydroxyethyl acrylate comprises 27–43% by weight composition, said 99% pure N,N'-methylenebisacrylamide 0.27%–0.42% by weight composition, said 2,2'-Azobis(2-(2-imidazolin-2-yl)propane) dihydrochloride comprises 0.02%–0.04% by weight composition, said deionized water comprises 56–72% by weight composition, and said cobalt chloride comprises 0.000005–0.06 grams per ml of said deionized water.

20. The fiber optic moisture sensor as recited in claim 15 wherein said superabsorbent polymer is a member chosen from acrylamides, acrylates, (meth)acrylates, and hydrogels.

21. The fiber optic moisture sensor as recited in claim 20 wherein said superabsorbent polymer is a cross-linked acrylate resin.

22. A method of making a fiber optic moisture sensor comprising the steps of:

synthesizing a self-supporting superabsorbent polymer;

casting a sensor head from said optically transparent superabsorbent polymer;

adjoining said sensor head to a means for transmitting light to and from said sensor head such that said sensor head is in direct optical communication with said means for transmitting light; and optically connecting a light detector to said means for transmitting light, said self supporting superabsorbent polymer supporting itself and said sensor head being devoid of any further support means.

23. A method as recited in claim 22, wherein said step of synthesizing said self-supporting superabsorbent polymer comprises mixing an acrylate resin, a polyacrylamide, a polymerization initiator, at least one solvent, and hydrochromic material.

24. A method as recited in claim 23, wherein said acrylate resin comprises 96% pure 2-hydroxyethyl acrylate, said polyacrylamide comprises 99% pure N,N'-methylenebisacrylamide, said polymerization initiator comprises 2,2'-Azobis(2-(2-imidazolin-2-yl)propane) dihydrochloride, said solvent comprises deionized water, and said hydrochromic material comprises cobalt chloride.

25. A method as recited in claim 24, wherein said 96% pure 2-hydroxyethyl acrylate comprises 27–43% by weight, said 99% pure N,N'-methylenebisacrylamide comprises 0.27%–0.42% by weight, said deionized water comprises 56–72% by weight, said 2,2'-Azobis(2-(2-imidazolin-2-yl)propane) dihydrochloride comprises 0.02%–0.04% by weight, and said cobalt chloride comprises 0.000005–0.06 grams per ml of said deionized water.

26. A method as recited in claim 22, wherein said superabsorbent polymer is a member chosen from acrylamides, acrylates, (meth)acrylates, and hydrogels.

27. A method as recited in claim 26, wherein said superabsorbent polymer is a cross-linked acrylate resin.

28. A method as recited in claim 22, wherein said self-supporting superabsorbent polymer is cast into a fiber.

29. A method as recited in claim 22, wherein said self-supporting superabsorbent polymer is cast into a cylinder.

* * * * *